US009516435B2

(12) United States Patent
Johnson

(10) Patent No.: US 9,516,435 B2
(45) Date of Patent: Dec. 6, 2016

(54) HEARING AID ADAPTER FOR EASY CONVERSION OF OPEN EAR TO CLOSED EAR FITTING

(71) Applicant: Earl Edward Johnson, Johnson City, TN (US)

(72) Inventor: Earl Edward Johnson, Johnson City, TN (US)

(73) Assignee: JOHNSON HEARING TECHNOLOGY AND COMMUNICATION, PLLC, Johnson City, TN (US)

( * ) Notice: Subject to any disclaimer, the term of this patent is extended or adjusted under 35 U.S.C. 154(b) by 0 days.

(21) Appl. No.: 13/914,811

(22) Filed: Jun. 11, 2013

(65) Prior Publication Data

US 2014/0270298 A1 Sep. 18, 2014

Related U.S. Application Data

(60) Provisional application No. 61/802,879, filed on Mar. 18, 2013.

(51) Int. Cl.

| | |
|---|---|
| ***H04R 25/00*** | (2006.01) |
| *H04R 1/00* | (2006.01) |
| *H04R 25/02* | (2006.01) |
| *A61B 7/02* | (2006.01) |

(52) U.S. Cl.
CPC .................................... *H04R 25/65* (2013.01)

(58) Field of Classification Search
CPC ..... H04R 25/658; H04R 25/65; H04R 25/652; H04R 25/656; H04R 25/60; H04R 2225/021; H04R 1/1016; H04R 2460/11; H04R 1/10; H04R 2460/09; H04R 2460/15; H04R 2225/025; H04R 2201/10
USPC ....... 381/328, 322, 323, 324, 330, 382, 380, 381/381, 379; 181/130, 135; 29/594
See application file for complete search history.

(56) References Cited

U.S. PATENT DOCUMENTS

| | | | | |
|---|---|---|---|---|
| 4,443,668 | A * | 4/1984 | Warren | 455/351 |
| 4,869,339 | A * | 9/1989 | Barton | 181/130 |
| 4,878,560 | A * | 11/1989 | Scott | 181/130 |
| 7,784,583 | B1 * | 8/2010 | Hall et al. | 181/130 |
| 2002/0085728 | A1 * | 7/2002 | Shennib et al. | 381/328 |
| 2005/0147269 | A1 * | 7/2005 | Oliveira et al. | 381/382 |
| 2007/0116309 | A1 * | 5/2007 | Smith | 381/313 |

* cited by examiner

*Primary Examiner* — Curtis Kuntz
*Assistant Examiner* — Sunita Joshi

(57) ABSTRACT

An open fitted hearing aid adapter allows a user to quickly transition between an open fitted style hearing aid and a closed fitted style hearing aid. This allows the user to conveniently benefit from the different advantages offered by both styles of hearing aids, according to the user's current needs. The open fitted hearing aid adapter has a custom ear mold, at least one receiving surface channel 19, and a tube securing mechanism. The receiving surface channel 19 is the component in which the open hearing aid component(s) (e.g., tubing, wiring, speaker, and/or microphone) of an open fitted hearing aid is positioned. The open hearing aid component(s) is positioned within the receiving surface channel 19 through a tubing slit, rather than being threaded through the custom ear mold and generally affixed in a permanent manner. The tube securing mechanism acts to hold the open hearing aid component(s) in place.

17 Claims, 15 Drawing Sheets

HEARING AID ADAPTER FOR EASY CONVERSION OF OPEN EAR TO CLOSED EAR FITTING

The current application claims a priority to the U.S. Provisional Patent application Ser. No. 61/802,879 filed on Mar. 18, 2013.

FIELD OF THE INVENTION

The present invention relates to hearing aids and generally to other assistive hearing devices that are worn at ear level. More specifically, the present invention provides a fitting that allows a user to easily transition or change from an open canal type hearing aid to a closed canal type hearing aid and vice versa; instead of the status quo, which has been to fit a hearing aid or assistive hearing device as either open or closed.

BACKGROUND OF THE INVENTION

Hearing aids have been used to assist those suffering from hearing loss since the 17th century. Many of the first designs were big and bulky and as such were not portable. Ear trumpets were later developed and were much more portable than previous options, yet they were still rather large. The first electronic hearing aid was introduced in the late 19th century, leading to the standard of electronic hearing aids used today. While several styles of hearing aids exist today, the majority can be classified into two categories, those that are open fitted and those that are closed fitted, with reference to the ear canal. The category of hearing aid used is dependent on the amount of hearing loss of the user, as well as preference of the end-user, as each style features benefits over the other. Open fitted hearing aids are worn behind the ear of the user (with varying speaker placements) and feature a small tube, either filled with air or electrical wiring, connected to rubber-like dome or tip and inserted into the ear canal of the user. This type of hearing aid leaves the ear canal open as much as possible which results in a minimal effect on ear canal resonances and thus reduces the occlusion effect (i.e., sound of the wearer's own voice is in a barrel), creating better comfort for the wearer. Open fitted hearing aids, however, are limited to wearers with less than severe high-frequency losses as they have an increased possibility of acoustic feedback and allow low frequency sounds to leak out of the ear canal. In comparison to open fitted hearing aids, closed fitted hearing aids exist as they can be custom fitted for each user with no limitation on hearing loss and can create an improved signal-to-noise ratio at the eardrum as a byproduct of hearing aid signal processing (i.e. directional microphone, noise reduction, and/or remote microphone technology). The improvement in signal-to-noise ratio creates better speech recognition in noise performance and perceived hearing aid benefit. Users of the open fitted type of hearing aid may suffer from feedback, where a whistling sound is caused by sound leaking and is amplified repeatedly. Whereas, users of closed fitted type hearing aids suffer from the occlusion effect. In certain situations one style of hearing aid may have advantages over the other, and in some cases users may own two separate hearing aid devices to receive the benefits of both.

Therefore, the object of the present invention is to provide an adapter that allows a user to transition from an open fitted hearing aid to a closed fitted hearing aid, and vice versa, in a matter of seconds. Thus the invention allows users to have the benefits of both an open and a closed fitting, depending on their hearing circumstance. The open fitted hearing aid adapter is custom designed and manufactured to fit the shape of an individual's ear much like a closed fitted hearing aid or ear mold attachment. The novelty of the adapter is its surface channel (e.g. cylindrical, rectangular or form-designed in shape). The channel is cut into the external surface of a custom ear mold to allow for the surface routed placement of open fitted hearing aid tubing, wiring, speakers, and/or microphones. In this way, a user can benefit from the advantages of a closed fitted hearing aid, while using his/her open fitted hearing aid by attaching the adapter. This invention differs from the existing conventional and ubiquitous attachment of an ear mold to hearing aid tubing, wiring, speakers, and/or microphones which is inserted through the core of the ear mold (i.e., approximate middle) and is generally affixed in a permanent state via adhesives, threading, total emersion, or other means. The functionality of this invention allows the user to easily switch from an open fitted hearing aid to a closed fitted hearing aid and vice versa, in a matter of seconds, by hearing aid components snapping into, or unsnapping from, the surface channel of the custom adapter.

DETAIL DESCRIPTIONS OF THE INVENTION

All illustrations of the drawings are for the purpose of describing selected versions of the present invention and are not intended to limit the scope of the present invention.

Figure 13:
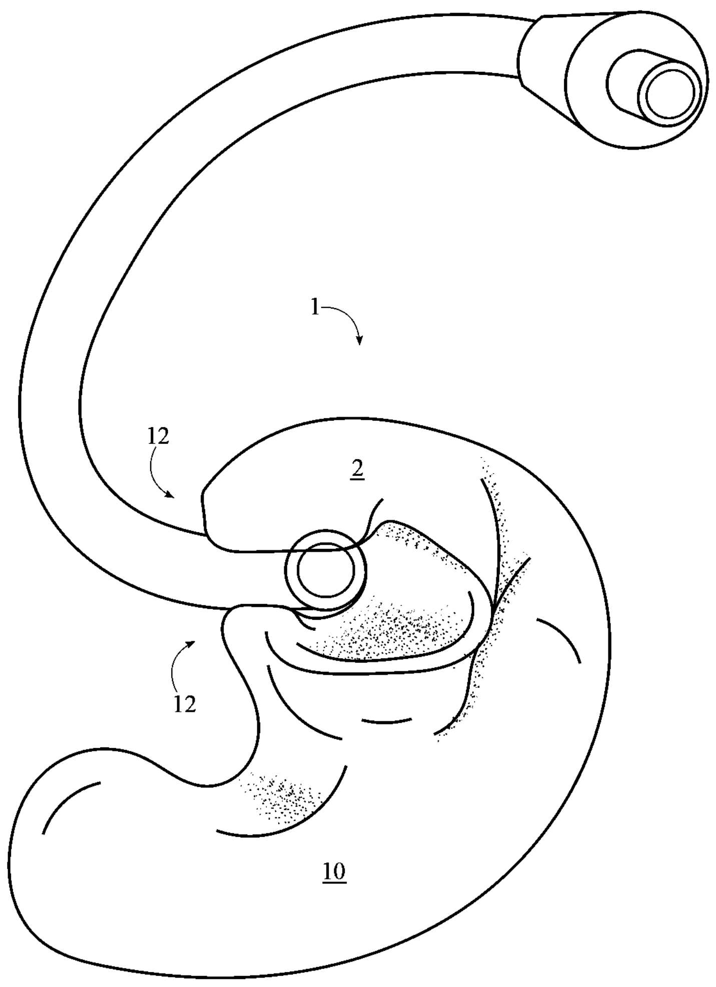
FIG. 13 is a perspective view of the custom ear mold having attached tubing.
Figure 14:
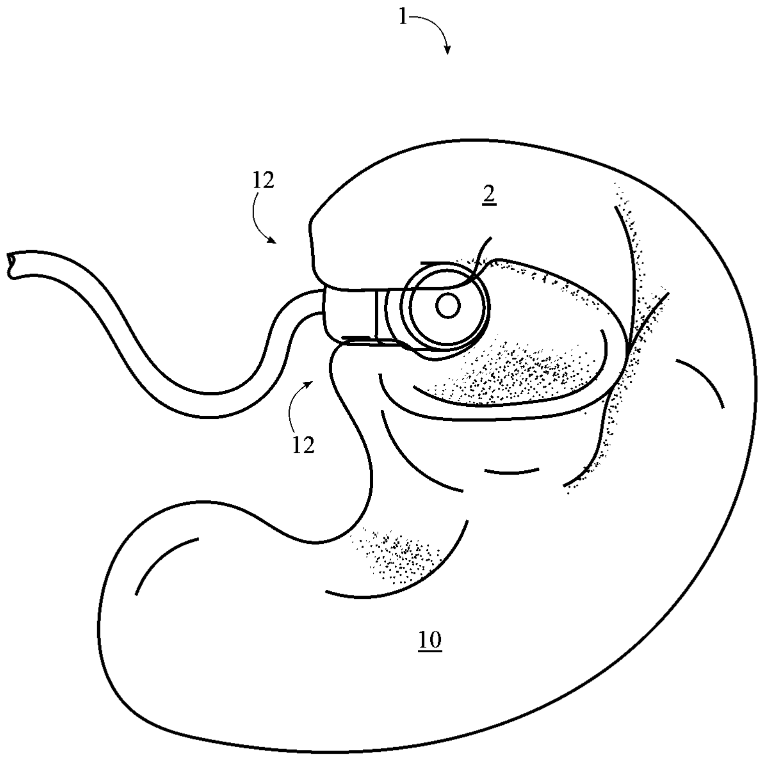
FIG. 14 is a perspective view of the custom ear mold having an attached receiver-in-the-canal wiring.

The present invention is an open fitted hearing aid adapter, which can be used to conveniently convert an open fitted hearing aid into a closed fitted hearing aid. In the preferred embodiment of the present invention, the open hearing aid component(s) of an open fitted hearing aid is attached to the open fitted hearing aid adapter, as shown in FIG. 13-14; however, any similar device may be attached. The open fitted hearing aid adapter comprises a custom ear mold 1, at least one receiving surface channel 19, and a tube securing mechanism 12. The custom ear mold 1 can be constructed from any material or combination of materials. Ideally, the custom ear mold 1 is uniquely designed to fit the individual shape of a user's ear. In this way, the custom ear mold 1 is able to provide the most comfortable fit for a user. However, it is also possible for the custom ear mold 1 to be designed such that one shape is capable of fitting the ear of multiple users. The at least one receiving surface channel 19 is the open space within the custom ear mold 1 that holds the open hearing aid component(s), such as ear mold tubing, wiring, speakers, and/or microphones. Once in place, the tube securing mechanism 12 prevents the open hearing aid component(s) from being inadvertently removed from the at least one receiving surface channel 19. The tube securing mechanism 12 can be constructed from any material or combination of materials and is ideally constructed using the same material as the custom ear mold 1.

In reference to FIG. 1-4, the custom ear mold 1 comprises a canal portion 2 and an outer-ear support body 10. The canal portion 2 is placed within a user's ear canal and thus is shaped to fit the user's ear canal. The outer-ear support body 10 is adjacently connected to the canal portion 2. In the preferred embodiment of the present invention, the outer-ear support body 10 is designed to rest within the concha of the user's ear; however, the outer-ear support body 10 may be designed to be placed in any portion of a user's outer ear. The outer-ear support body 10 provides stability to the canal portion 2, ensuring that the canal portion 2 remains in the proper position within the user's ear.

Figure 15:
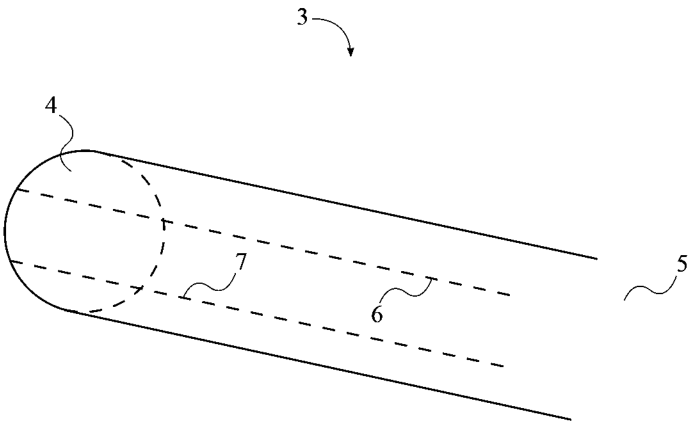
FIG. 15 is a perspective view of the tubing guide in the preferred embodiment of the present invention.

In reference to FIG. 1-4 and FIG. 13-14, the at least one receiving surface channel 19 traverses though the canal portion 2 creating a conduit leading from the inner ear to the outer surface of the custom ear mold 1. In this way, the at least one receiving surface channel cradles the open hearing aid component(s) and directs the open hearing aid component(s) within the user's ear canal. The at least one receiving surface channel 19 comprises a tubing guide 3, a receiving volume 9, and a tubing slit 8. The tubing guide 3 is positioned along the canal portion 2 and defines the shape, positioning, and direction of the receiving volume 9. The tubing guide 3 comprises an open outer end 4, an open canal end 5, a first guide line 6, and a second guide line 7, as shown in FIG. 15. The open outer end 4 and the open canal end 5 are positioned opposite of each other along the tubing guide 3. In this way, the open outer end 4 and the open canal end 5 provide the bounds between which the at least one receiving surface channel 19 traverses the canal portion 2.

The open outer end 4 traverses through the exterior surface of the custom ear mold 1, and determines the angle at which the open hearing aid component(s) extends from the custom ear mold 1 to the open fitted hearing aid. The open canal end 5 traverses through the interior surface of the custom ear mold 1, and determines the angle at which the open hearing aid component(s) is positioned within the user's ear canal.

In reference to FIG. 1-4, the at least one receiving surface channel 19 is cut along the canal portion 2 and creates the open space used to position the open hearing aid component(s). The receiving volume 9 is a passage of cubic dimension that is cut through the canal portion 2 and provides the open space in which the open hearing aid component rests. The receiving volume 9 is delineated, both longitudinally and cross-sectionally, by the tubing guide 3. In the preferred embodiment of the present invention, the lateral cross section of the tubing guide 3 is circular, such that the at least one receiving surface channel 19 can accommodate the circular tube-like member of a typical open fitted hearing aid. However, the tubing guide 3 can be any other shape, such that the at least one receiving surface channel 19 may accommodate various types of open fitting hearing aid component inserts.

In reference to FIG. 1-4, an open slot is created along the canal portion 2 through which the open hearing aid component can be inserted into the canal portion 2. This open slot is created by the tubing slit 8. The tubing slit 8 is positioned along the tubing guide 3 in between the open outer end 4 and the open canal end 5. In this way, the tubing slit 8 traverses along the entirety of both the tubing guide 3 and the receiving volume 9. The tubing slit 8 laterally traverses through the tubing guide 3 into the receiving volume 9. The created open slot traverses the canal portion 2 and extends from the outer surface of the canal portion 2 into the inner receiving volume 9. As a result, the tubing slit 8 allows a length of the open hearing aid component(s) to be snapped into place within the at least one receiving surface channel 19, as opposed to the conventional method of threading, gluing, embedding or otherwise more permanently affixing tubing through an ear mold. This allows for open fitted hearing aid components to more readily be attached or detached from the open fitted hearing aid adapter.

When the open hearing aid component(s) is positioned within the at least one receiving surface channel 19, the tube securing mechanism 12 holds the open hearing aid component in place. In reference to FIG. 6-8, the first guide line 6 and the second guide line 7 are used to define the placement of the tube securing mechanism 12 along the at least one receiving surface channel 19. As such, the first guide line 6 and the second guide line 7 are delineated by the tubing slit 8. This ensures that the tube securing mechanism 12 is positioned along the tubing slit 8. The placement of the tube securing mechanism 12 along the tubing slit 8 is essential, as the tube securing mechanism 12 locks the open hearing aid component in place within the receiving volume 9 of the at least one receiving surface channel 19. The first guide line 6 and the second guide line 7 are positioned opposite of each other across the tubing slit 8, one being positioned along the top of the tubing slit 8 and the other along the bottom of the tubing slit 8. This allows the tube securing mechanism 12 to secure the open hearing aid component from one or both sides of the tubing slit 8.

Figure 1:
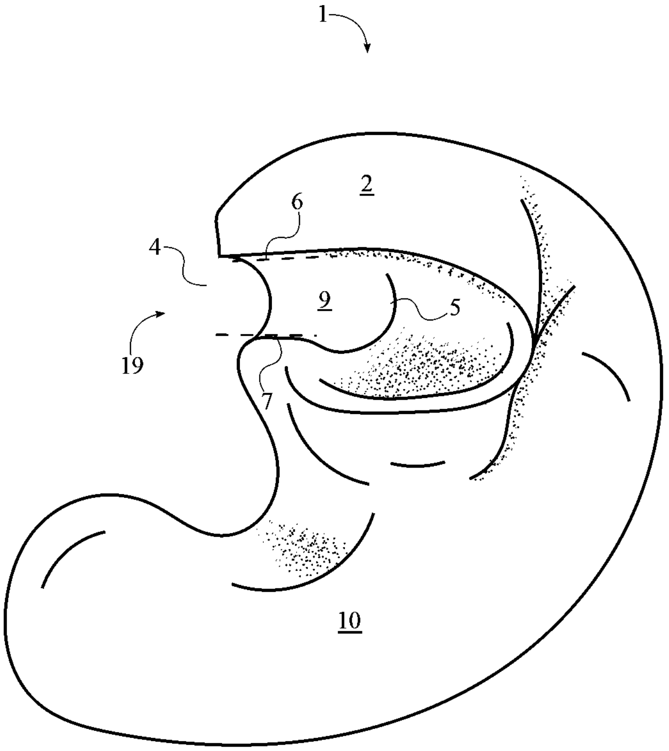
FIG. 1 is a perspective view of the custom ear mold in the preferred embodiment of the present invention.
Figure 2:
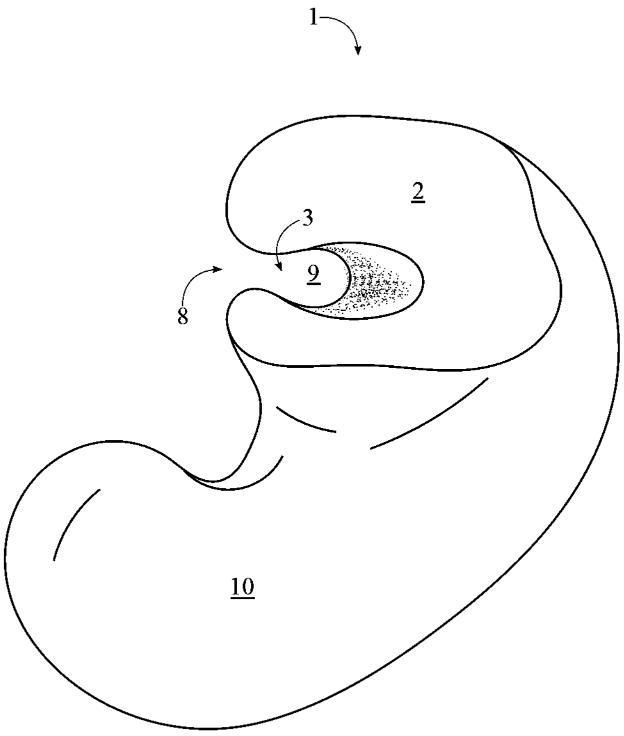
FIG. 2 is a front elevational view of the custom ear mold in the preferred embodiment of the present invention.
Figure 3:
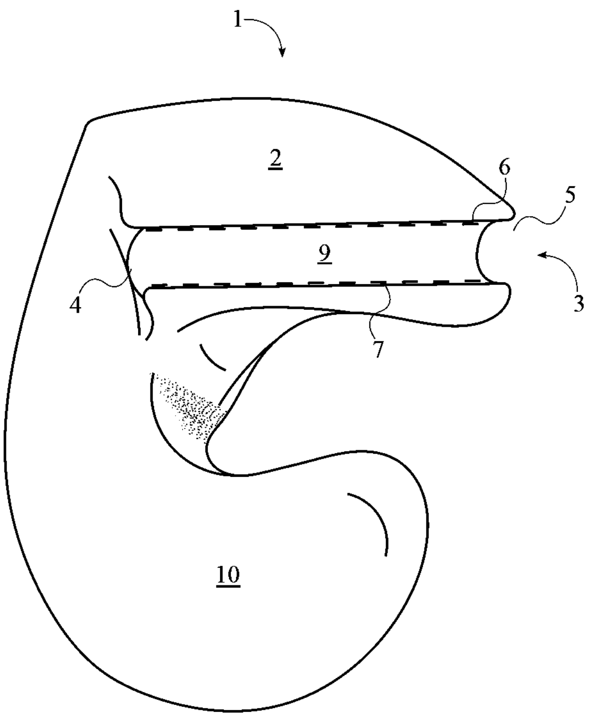
FIG. 3 is a left side elevational view of the custom ear mold in the preferred embodiment of the present invention.
Figure 4:
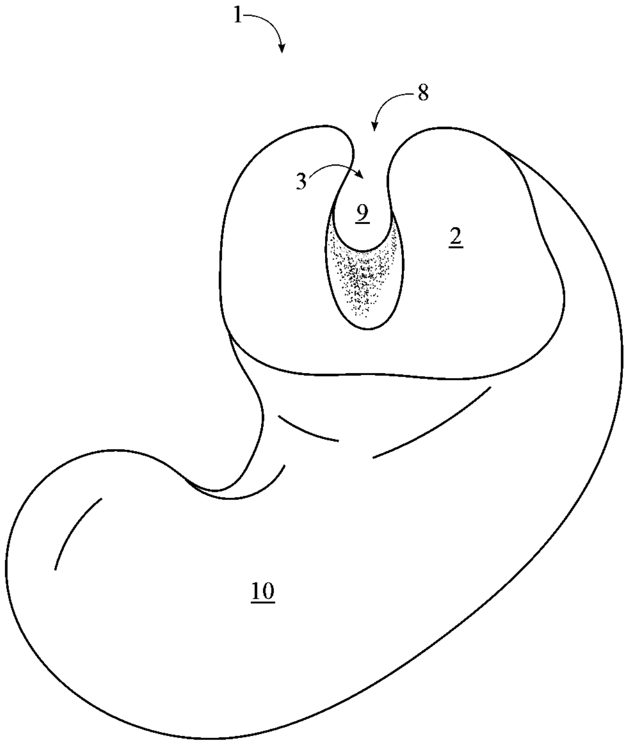
FIG. 4 is a front elevational view of the custom ear mold having an alternative positioned tubing slit.
Figure 5:
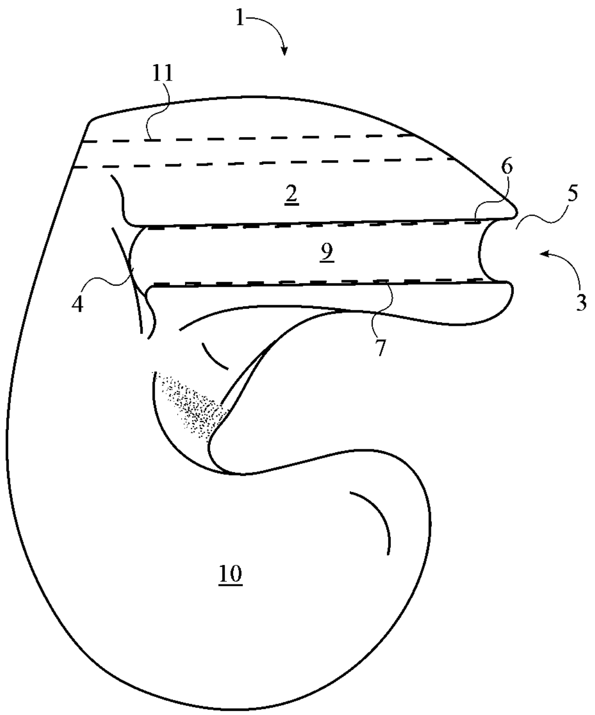
FIG. 5 is a left side elevational view of the custom ear mold having a ventilation channel.

In reference to FIG. 5, in one embodiment of the present invention, the canal portion 2 further comprises a ventilation channel 11. The ventilation channel 11 is optional as a means to offer a hearing aid style that is in between a closed canal fitting and an open canal fitting. The ventilation channel 11 is a recess having a circular cross section that traverses through the canal portion 2. The ventilation channel 11 is positioned along the canal portion 2, adjacent to the at least one receiving surface channel 19, and has a first open end adjacent to the open outer end 4 and a second open end adjacent to the open canal end 5. The ventilation channel 11 is an additional passage into the user's ear canal that can be used to influence or prevent feedback from the open fitted hearing aid, and/or to offer pressure equalization.

Figure 6:
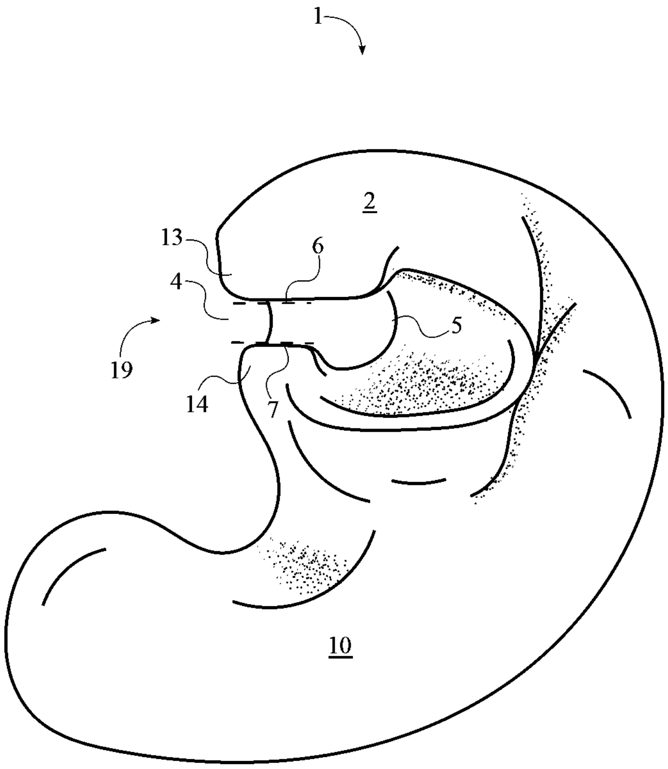
FIG. 6 is a perspective view of the tube securing mechanism having a first edge lip and a second edge lip.

In reference to FIG. 6, in one embodiment of the present invention, the tube securing mechanism 12 comprises a first edge lip 13 and a second edge lip 14. The first edge lip 13 and the second edge lip 14 are adjacently connected to the canal portion 2.

The first edge lip 13 being positioned along the first guide line 6 and the second edge lip 14 being positioned along the second guide line 7. The first edge lip 13 and the second edge lip 14 are protrusions positioned across the at least one receiving surface channel 19 and are directed towards each other, such that they secure the open hearing aid component(s) along both sides of the tubing slit 8. The first edge lip 13 and the second edge lip 14 are semi-rigid members used to retain the open hearing aid component(s) within the receiving surface channel 19. The first edge lip 13 and the second edge lip 14 bend inwards or outwards when sufficient force is applied as to allow the open hearing aid component(s) to be placed within or removed from the at least one receiving surface channel 19. When the open hearing aid component(s) is at rest within the at least one receiving surface channel 19, the first edge lip 13 and the second edge lip 14 provide rigid support to prevent the open hearing aid component(s) from inadvertently being removed.

Figure 7:
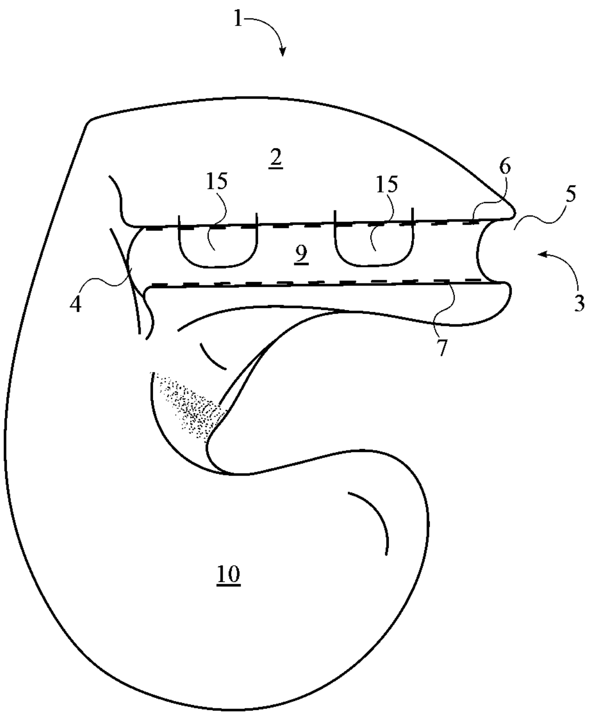
FIG. 7 is a left side elevational view of the tube securing mechanism having a plurality of hooks connected along the first guide line.
Figure 8:
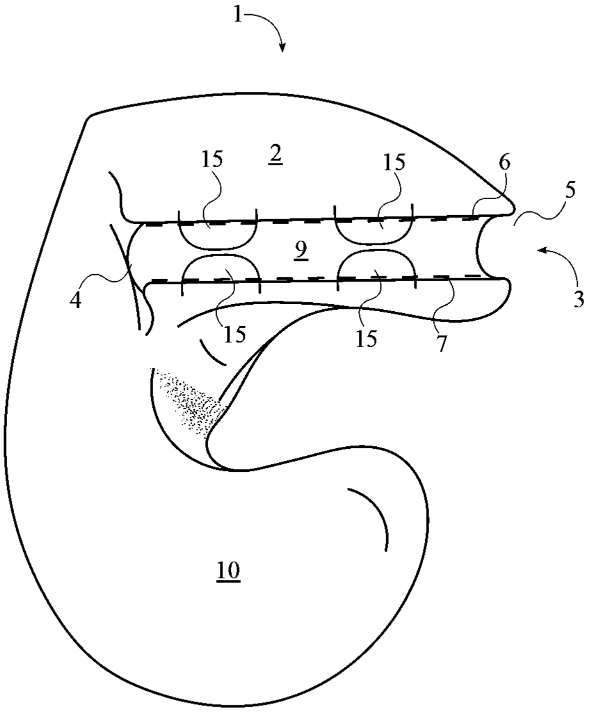
FIG. 8 is a left side elevational view of the tube securing mechanism having the plurality of hooks connected along both the first guide line and the second guide line.

In reference to FIG. 7-8, in other embodiments of the present invention, the tube securing mechanism 12 comprises a plurality of hooks 15. The plurality of hooks 15 is adjacently connected to the canal portion 2. Each of the plurality of hooks 15 is a semi-rigid member used to retain the open hearing aid component(s) within the at least one receiving surface channel 19. Each of the plurality of hooks 15 overhangs the tubing slit 8 and bends inwards or outwards when sufficient force is applied, as to allow the open hearing aid component(s) to be placed within or removed from the at least one receiving surface channel 19. When the open hearing aid component(s) is at rest within the at least one receiving surface channel 19, the plurality of hooks 15 provides rigid support to prevent the open hearing aid component(s) from inadvertently being removed. The plurality of hooks 15 can be positioned along the canal portion 2 in multiple configurations. In one embodiment of the present invention, the plurality of hooks 15 is positioned along the first guide line 6, as shown in FIG. 7. In this way, the plurality of hooks 15 secures the open hearing aid component(s) within the at least one receiving surface channel 19 from only one side of the tubing slit 8. In another embodiment of the present invention, the plurality of hooks 15 is positioned along both the first guide line 6 and the second guide line 7, as shown in FIG. 8. In this way, the plurality of hooks 15 secures the open hearing aid component(s) within the at least one receiving surface channel 19 from both sides of the tubing slit 8.

Figure 9:
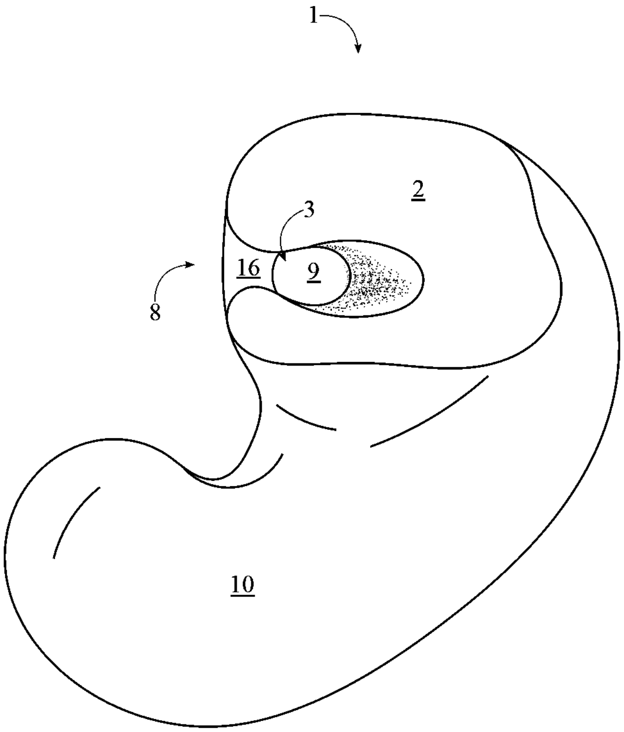
FIG. 9 is a front elevational view of the tube securing mechanism having an access panel attached to the canal portion.
Figure 10:
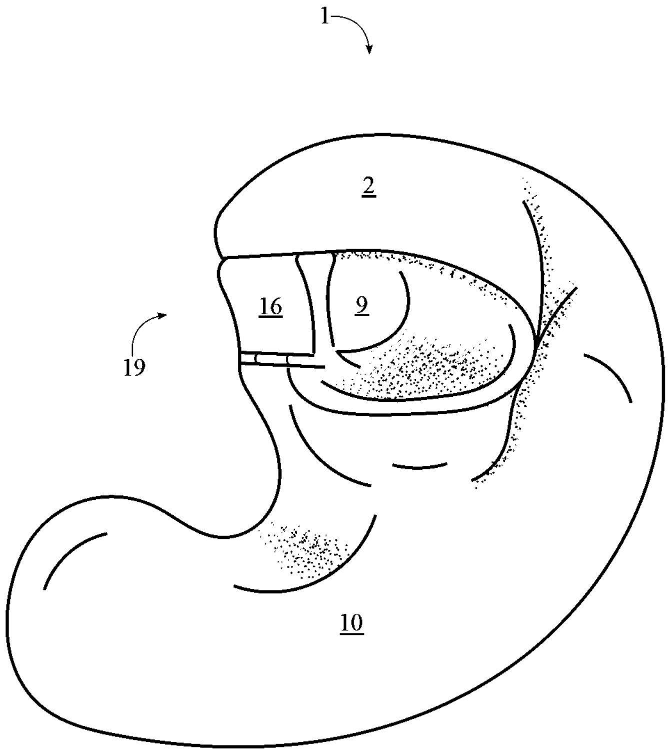
FIG. 10 is a perspective view of the tube securing mechanism having an access panel hingedly connected to the canal portion.

In reference to FIG. 9-10, in other embodiments of the present invention, the tube securing mechanism 12 comprises an access panel 16. The access panel 16 is positioned within the tubing slit 8 in order to fully enclose the open hearing aid component(s) within the receiving volume 9. This ensures the open hearing aid component(s) is secured along the entire length of the at least one receiving surface channel 19. The access panel 16 can be held in place within the tubing slit 8 using any means of attachment, such as a snap fit or frictional fit. The access panel 16 can be removed from the at least one receiving surface channel 19 in order to allow passage of the open hearing aid component(s) through the tubing slit 8. In one embodiment of the present invention, the access panel 16 is hingedly connected to the canal portion 2, as shown in FIG. 10. This ensures that the access panel 16 is not misplaced or lost when it is removed from the at least one receiving surface channel 19. In another embodiment of the present invention, the access panel 16 is attached to the canal portion 2, such that it may be completely detached from the canal portion 2. This allows the access panel 16 to be replaced, as well as ensures that the access panel 16 does not interfere with the passage of the open hearing aid component(s) through the tubing slit 8.

Figure 11:
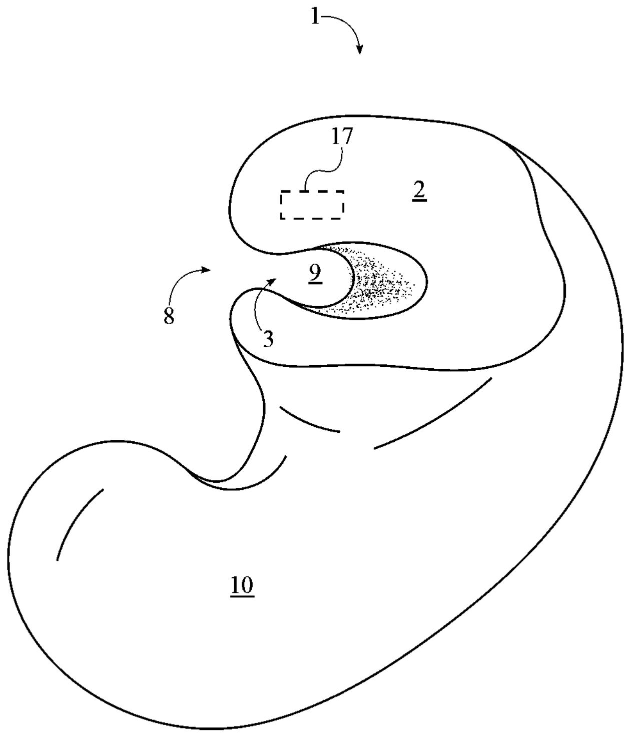
FIG. 11 is a front elevational view of the tube securing mechanism having a magnet positioned within the canal portion.
Figure 12:
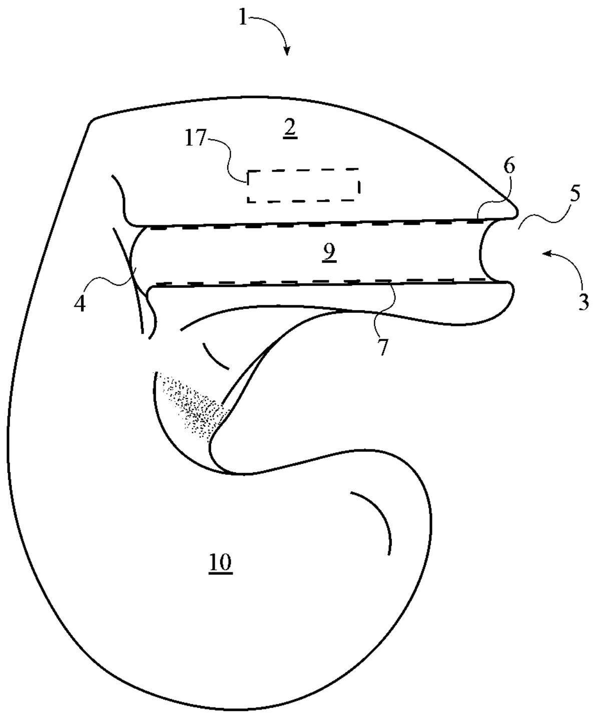
FIG. 12 is a left side elevational view of the tube securing mechanism having a magnet positioned within the canal portion.

In reference to FIG. 11-12, in another embodiment of the present invention, the tube securing member comprises at least one magnet 17. The tube securing member is positioned within the canal portion 2 and is positioned about the at least one receiving surface channel 19. The at least one magnet 17 produces a magnetic field, which can be used to secure or couple objects with metallic properties. When a metallic device, such as the receiver-in-the-canal wiring or receiver itself, is positioned within the at least one receiving surface channel 19, it is held in place by the magnetic force of the at least one magnet 17. The at least one magnet 17 provides enough force to securely hold the metallic device in place, while allowing the user to readily remove it if necessary.

Although the invention has been explained in relation to its preferred embodiment, it is to be understood that many other possible modifications and variations can be made without departing from the spirit and scope of the invention as hereinafter claimed.

What is claimed is:

1. An open fitted hearing aid adapter comprises:
- a custom ear mold;
- an at least one receiving surface channel;
- a tube securing mechanism;
- the custom ear mold comprises a canal portion and an outer-ear support body;
- each of the at least one receiving surface channel comprises a tubing guide, a tubing slit, and a receiving volume;
- the tubing guide comprises an open outer end, an open canal end, a first guide line and a second guide line;
- the outer-ear support body being adjacently connected to the canal portion;
- the at least one receiving surface channel traversing through the canal portion;
- the tubing guide being positioned along the canal portion;
- the open outer end and the open canal end being positioned opposite of each other along the tubing guide;
- the receiving volume being delineated by the tubing guide;
- the tubing slit being positioned along the tubing guide in between the open outer end and the open canal end; and
- the tubing slit laterally traversing through the tubing guide into the receiving volume.

2. The open fitted hearing aid adapter as claimed in claim 1 comprises:
- the first guide line and the second guide line being delineated by the tubing slit; and
- the first guide line and the second guide line being positioned opposite of each other across the tubing slit.

3. The open fitted hearing aid adapter as claimed in claim 1 comprises:
- the tube securing mechanism comprises a first edge lip and a second edge lip;
- the first edge lip and the second edge lip being adjacently connected to the canal portion;
- the first edge lip being positioned along the first guide line; and
- the second edge lip being positioned along the second guide line.

4. The open fitted hearing aid adapter as claimed in claim 1 comprises:
the tube securing mechanism comprises a plurality of hooks; and
the plurality of hooks being adjacently connected to the canal portion.

5. The open fitted hearing aid adapter as claimed in claim 4 comprises:
the plurality of hooks being positioned along the first guide line.

6. The open fitted hearing aid adapter as claimed in claim 4 comprises:
the plurality of hooks being positioned along both the first guide line and the second guide line.

7. The open fitted hearing aid adapter as claimed in claim 1 comprises:
the tube securing mechanism comprises an access panel; and
the access panel being positioned within the tubing slit.

8. The open fitted hearing aid adapter as claimed in claim 7 comprises:
the access panel being hingedly connected to the canal portion.

9. The open fitted hearing aid adapter as claimed in claim 7 comprises:
the access panel being attached to the canal portion, wherein the access panel can be detached from the canal portion.

10. The open fitted hearing aid adapter as claimed in claim 1 comprises:
the tube securing mechanism comprises an at least one magnet;
the at least one magnet being positioned within the canal portion; and
the at least one magnet being positioned about the at least one receiving surface channel.

11. The open fitted hearing aid adapter as claimed in claim 1 comprises:
the canal portion further comprises a ventilation channel;
the ventilation channel being positioned along the canal portion;
the ventilation channel being positioned adjacent to the at least one receiving surface channel; and
the ventilation channel traversing through the canal portion.

12. An open fitted hearing aid adapter comprises:
a custom ear mold;
an at least one receiving surface channel;
a tube securing mechanism;
the custom ear mold comprises a canal portion and an outer-ear support body;
each of the at least one receiving surface channel comprises a tubing guide, a tubing slit, and a receiving volume;
the tube securing mechanism comprises a first edge lip and a second edge lip;
the tubing guide comprises an open outer end, an open canal end, a first guide line and a second guide line;
the outer-ear support body being adjacently connected to the canal portion;
the at least one receiving surface channel traversing through the canal portion;
the tubing guide being positioned along the canal portion;
the open outer end and the open canal end being positioned opposite of each other along the tubing guide;
the receiving volume being delineated by the tubing guide;

the tubing slit being positioned along the tubing guide in between the open outer end and the open canal end; and
the tubing slit laterally traversing through the canal portion and the tubing guide into the receiving volume.

13. The open fitted hearing aid adapter as claimed in claim 12 comprises:
the first guide line and the second guide line being delineated by the tubing slit;
the first guide line and the second guide line being positioned opposite of each other across the tubing slit;
the first edge lip and the second edge lip being adjacently connected to the canal portion;
the first edge lip being positioned along the first guide line; and
the second edge lip being positioned along the second guide line.

14. The open fitted hearing aid adapter as claimed in claim 12 comprises:
the canal portion further comprises a ventilation channel;
the ventilation channel being positioned along the canal portion;
the ventilation channel being positioned adjacent to the at least one receiving surface channel; and
the ventilation channel traversing through the canal portion.

15. An open fitted hearing aid adapter comprises:
a custom ear mold;
an at least one receiving surface channel;
a tube securing mechanism;
the custom ear mold comprises a canal portion and an outer-ear support body;
each of the at least one receiving surface channel comprises a tubing guide, a tubing slit, and a receiving volume;
the tube securing mechanism comprises an at least one magnet;
the tubing guide comprises an open outer end and an open canal end;
the outer-ear support body being adjacently connected to the canal portion;
the at least one receiving surface channel traversing through the canal portion;
the tubing guide being positioned along the canal portion;
the open outer end and the open canal end being positioned opposite of each other along the tubing guide;
the receiving volume being delineated by the tubing guide;
the tubing slit being positioned along the tubing guide in between the open outer end and the open canal end; and
the tubing slit laterally traversing through the canal portion and the tubing guide into the receiving volume.

16. The open fitted hearing aid adapter as claimed in claim 15 comprises:
the at least one magnet being positioned within the canal portion; and
the at least one magnet being positioned about the at least one receiving surface channel.

17. The open fitted hearing aid adapter as claimed in claim 15 comprises:
the canal portion further comprises a ventilation channel;
the ventilation channel being positioned along the canal portion;

the ventilation channel being positioned adjacent to the at least one receiving surface channel; and the ventilation channel traversing through the canal portion.

* * * * *